US00PP32131P2

(12) United States Plant Patent
Bernuetz

(10) Patent No.: US PP32,131 P2
(45) Date of Patent: Aug. 25, 2020

(54) ***ARGYRANTHEMUM* PLANT NAMED 'BONMAD 1498'**

(50) Latin Name: ***Argyranthemum* X *hybrida***
Varietal Denomination: Bonmad 1498

(71) Applicant: Andrew Bernuetz, Silverdale (AU)

(72) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 16/602,284

(22) Filed: Sep. 6, 2019

(51) Int. Cl.
*A01H 6/14* (2018.01)

(52) U.S. Cl.
USPC ..... Plt./406
CPC ..... *A01H 6/14* (2018.05)

(58) Field of Classification Search
USPC ..... Plt./406
CPC ..... A01H 5/02
See application file for complete search history.

(56) References Cited

PUBLICATIONS

PLUTO UPOVROM Plant Variety Database Citation for 'Bonmad 1498' as per JP PBR 33802; Jun. 18, 2019; 1 page.*

* cited by examiner

*Primary Examiner* — Kent L Bell
(74) *Attorney, Agent, or Firm* — C. A. Whealy

(57) ABSTRACT

A new and distinct cultivar of *Argyranthemum* plant named 'Bonmad 1498', characterized by its compact, upright, uniform and mounded plant habit; vigorous growth habit; early and freely flowering habit; semi-double-type inflorescences with ray florets that are initially light yellow in color with development becoming deep pink to moderately purplish pink and pale yellow in color and yellow orange-colored disc florets; and good garden performance.

2 Drawing Sheets

Figure 1:
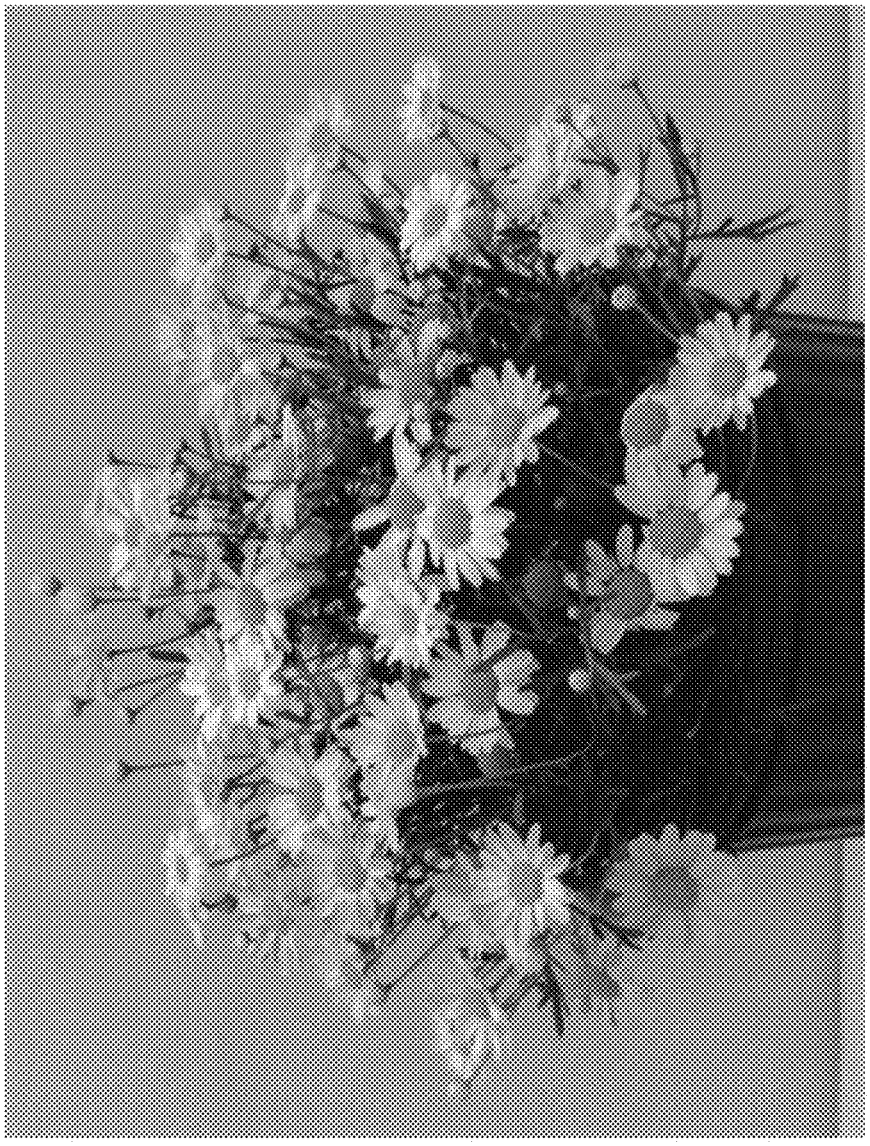

Botanical designation: *Argyranthemum* x *hybrida*.
Cultivar denomination: 'BONMAD 1498'.

BACKGROUND OF THE INVENTION

The present invention relates to a new and distinct cultivar of *Argyranthemum* plant, botanically known as *Argyranthemum* x *hybrida* and hereinafter referred to by the name 'Bonmad 1498'.

The objective of the breeding program is to create new compact and freely flowering *Argyranthemum* plants with attractive floret colors and good garden performance.

The new *Argyranthemum* plant originated from a cross-pollination made by the Inventor in 2012 in Yellow Rock, New South Wales, Australia of a proprietary selection of *Argyranthemum* x *hybrida* identified as code number 11-316, not patented, as the female, or seed, parent with a mixture of pollen from 13 unidentified proprietary selections of *Argyranthemum* x *hybrida*, as the male, or pollen, parent. The new *Argyranthemum* was discovered and selected by the Inventor as a single flowering plant within the progeny of the stated cross-pollination in a controlled environment in Yellow Rock, New South Wales, Australia in June, 2014.

Asexual reproduction of the new *Argyranthemum* plant by vegetative tip cuttings was first conducted in Yellow Rock, New South Wales, Australia in June, 2014. Asexual reproduction by cuttings has shown that the unique features of this new *Argyranthemum* plant are stable and reproduced true to type in successive generations.

SUMMARY OF THE INVENTION

Plants of the new *Argyranthemum* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Bonmad 1498'. These characteristics in combination distinguish 'Bonmad 1498' as a new and distinct *Argyranthemum* cultivar:

1. Compact, upright, uniform and mounded plant habit.
2. Vigorous growth habit.
3. Early and freely flowering habit.
4. Semi-double-type inflorescences with ray florets that are initially light yellow in color with development becoming deep pink to moderately purplish pink and pale yellow in color and yellow orange-colored disc florets.
5. Good garden performance.

Plants of the new *Argyranthemum* differ from plants of the female parent selection in ray floret color. Ray florets of plants of the new *Argyranthemum* are initially light yellow in color with development becoming deep pink to moderately purplish pink and pale yellow in color whereas ray florets of plants of the female parent selection are red in color.

Plants of the new *Argyranthemum* differ from plants of the male parent selections in ray floret color. Ray florets of plants of the new *Argyranthemum* are initially light yellow in color with development becoming deep pink to moderately purplish pink and pale yellow in color whereas ray florets of plants of the 13 male parent selections are either yellow, pink or red in color.

Plants of the new *Argyranthemum* can be compared to plants of the *Argyranthemum* x *hybrida* 'Bonmadhopi', not patented. In side-by-side comparisons, plants of the new *Argyranthemum* differ from plants of 'Bonmadhopi' in the following characteristics:

1. Plants of the new *Argyranthemum* are taller and broader than plants of 'Bonmadhopi'.
2. Plants of the new *Argyranthemum* have smaller leaves than plants of 'Bonmadhopi'.
3. Inflorescences of plants of the new *Argyranthemum* are semi-double types whereas inflorescences of plants of 'Bonmadhopi' are single-types.
4. Ray florets of plants of the new *Argyranthemum* are initially light yellow in color with development becoming deep pink to moderately purplish pink and pale yellow in color whereas ray florets of plants of 'Bonmadhopi' are red purple and white in color.

BRIEF DESCRIPTION OF THE PHOTOGRAPHS

The accompanying photographs illustrate the overall appearance of the new *Argyranthemum* plant. These photographs show the colors as true as it is reasonably possible to obtain in colored reproductions of this type. Colors in the photographs may differ slightly from the color values cited in the detailed botanical description which accurately describe the colors of the new *Argyranthemum* plant.

The photograph on the first sheet (FIG. 1 of 2) is a side perspective view of a typical flowering plant of 'Bonmad 1498' grown in a container.

Figure 2:
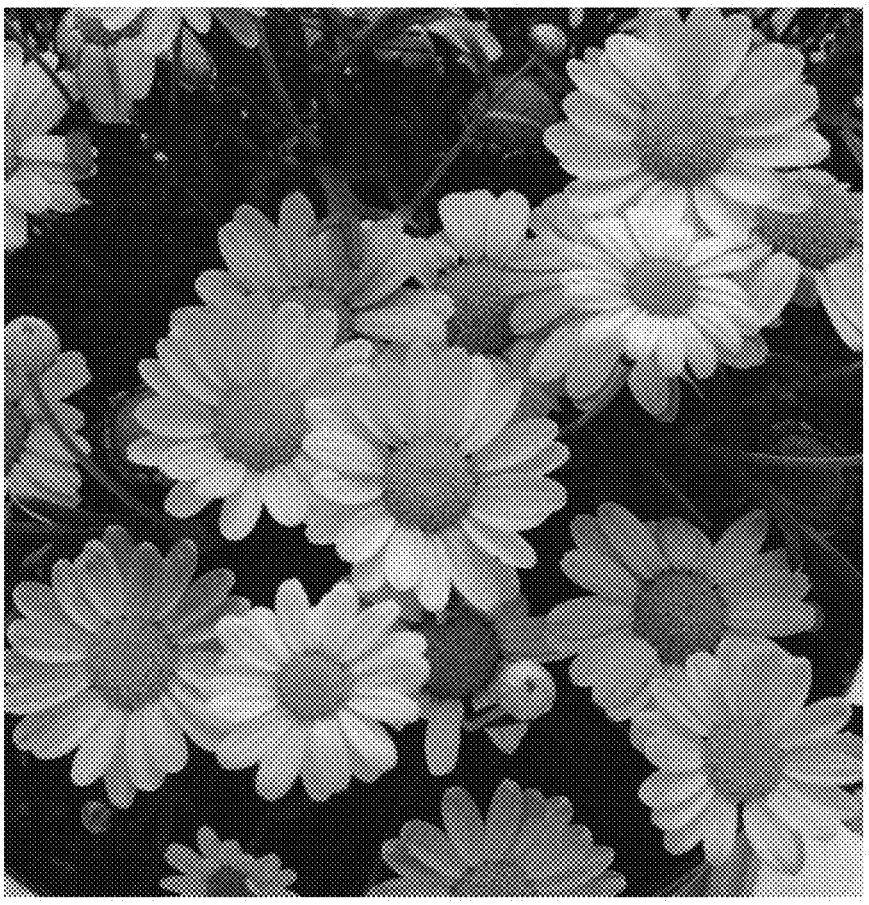

The photograph on the second sheet (FIG. 2 of 2) is a close view of a typical flowering plant of 'Bonmad 1498'.

DETAILED BOTANICAL DESCRIPTION

The aforementioned photographs and following observations and measurements describe plants grown during the spring in Higashiomi, Shiga, Japan in an outdoor nursery and under conditions and practices which approximate those generally used in commercial potted *Argyranthemum* production. During the production of the plants, day temperatures averaged 23° C. and night temperatures averaged 13° C. Plants used in the photographs were four months old and plants used for the detailed description were five months old. In the following description, color references are made to The Royal Horticultural Society Colour Chart, 2001 Edition, except where general terms of ordinary dictionary significance are used.

Botanical classification: *Argyranthemum* x *hybrida* 'Bonmad 1498'.

Parentage:

*Female, or seed, parent*.—Proprietary selection of *Argyranthemum* x *hybrida* identified as code number 11-316, not patented.

*Male, or pollen, parent*.—Pollen mixture from 13 unidentified proprietary selection of *Argyranthemum* x *hybrida*, not patented.

Propagation:

*Type*.—By vegetative terminal cuttings.

*Time to initiate roots, summer and winter*.—About six to nine days at temperatures of about 20° C. to 25° C.

*Time to produce a rooted young plant, summer and winter*.—About three weeks at temperatures of about 20° C. to 25° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous semi-double-type potted *Argyranthemum*; compact, upright, uniform and mounded plant habit; strong and freely branching growth habit with about four to five primary lateral branches developing per plant; dense and full plants; pinching will enhance lateral branching; vigorous growth habit.

*Plant height*.—About 30 cm.

*Plant diameter*.—About 40 cm.

*Lateral branches*.—Length: About 4.6 cm. Diameter: About 4.7 mm. Internode length: About 8 mm. Strength: Strong; young stems, flexible. Aspect: Upright to somewhat outwardly. Texture: Smooth, glabrous. Color: Close to 145B.

Foliage description:

*Arrangement*.—Alternate, simple.

*Length*.—About 4 cm.

*Width*.—About 3.4 cm.

*Lateral lobe length*.—About 2.3 cm.

*Lateral lobe width*.—About 6.8 mm.

*Lateral lobe depth of incision*.—About 2 cm.

*Shape*.—Obovate, palmately-parted.

*Apex*.—Acute.

*Base*.—Cuneate.

*Margin*.—Palmately-parted.

*Texture, upper and lower surfaces*.—Smooth, glabrous.

*Venation*.—Pinnate, reticulate.

*Color*.—Developing leaves, upper surface: Close to 137C. Developing leaves, lower surface: Close to 137D. Fully expanded leaves, upper surface: Close to 137B; venation, close to 138A. Fully expanded leaves, lower surface: Close to 137C; venation, close to 138A.

*Petioles*.—Length: About 1.1 cm. Diameter: About 2.8 mm. Texture, upper and lower surfaces: Smooth, glabrous. Color, upper surface: Close to 137B. Color, lower surface: Close to 137C.

Inflorescence description:

*Appearance*.—Semi-double-type inflorescence form with elliptic-shaped ray florets and tubular disc florets; solitary upright inflorescences borne on terminals above foliar plane; ray and disc florets arranged acropetally on a capitulum.

*Fragrance*.—None detected.

*Flowering season and response*.—Plants flower from spring through late autumn in Japan; flowering continuous during this period; early flowering habit, plants begin flowering about twelve weeks after sticking unrooted cuttings.

*Inflorescence longevity*.—Inflorescences last about two weeks on the plant; inflorescences persistent.

*Quantity of inflorescences*.—Freely flowering habit with numerous inflorescences developing per lateral branch.

*Inflorescence buds*.—Height: About 1.3 cm. Diameter: About 1.1 cm. Shape: Globose. Color: Distally, close to 51D; proximally, close to 4C.

*Inflorescence size*.—Diameter: About 4.4 cm. Depth (height): About 1.3 cm. Diameter of disc: About 1.4 cm.

*Ray florets*.—Quantity and arrangement: About 22 ray florets arranged in one to two whorls; ray florets imbricate. Length: About 1.5 cm. Width: About 7.3 mm. Shape: Elliptic. Apex: Rounded, occasionally emarginate or retuse. Base: Cuneate to attenuate. Margin: Entire. Texture, upper and lower surfaces: Glabrous; longitudinally ribbed. Color: When opening, upper surface: Close to 4C. When opening, lower surface: Close to 54C; towards the base, close to 4C. Fully opened, upper surface: Close to 39C and 51C; with development, a mixture of close to 54D and 4D; venation, similar to lamina colors. Fully opened, lower surface: Close to 51D; venation, close to 51D; color does not change with development.

*Disc florets*.—Quantity and arrangement: About 150 massed at center of receptacle in numerous whorls. Shape: Tubular. Apex: Acute, five-pointed. Length: About 5 mm. Diameter: About 1.9 mm. Color, immature and mature: Close to between 14A to 21A.

*Phyllaries*.—Quantity and arrangement: About 21 arranged in several whorls; phyllaries imbricate. Involucral diameter: About 1.2 cm. Length: About 4 mm. Width: About 2.8 mm. Shape: Lanceolate. Apex: Acute. Base: Truncate, fused. Margin: Entire. Texture, upper and lower surfaces: Smooth, glabrous. Color, upper and lower surfaces: Close to 144A.

*Peduncles*.—Length: About 6.9 cm. Diameter: About 1.3 cm. Aspect: Mostly upright. Strength: Strong, flexible. Texture: Smooth, glabrous. Color: Close to 138A.

*Reproductive organs*.—Androecium: Present on disc florets only. Quantity per floret: About five. Anther shape: Ellipsoidal. Anther color: Close to 13A. Pollen amount: Moderate. Pollen color: Close to 17B. Gynoecium: Present on both ray and disc florets. Quantity per floret: One. Pistil length: About 4.2 mm. Stigma shape: Bi-parted. Stigma color: Close to 13A. Ovary color: Close to 154C.

*Seeds and fruits*.—To date, seed and fruit production have not been observed on plants of the new *Argyranthemum*.

Pathogen & pest resistance: To date, resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about 0° C. to about 35° C.

It is claimed:

1. A new and distinct *Argyranthemum* plant named 'Bonmad 1498' as illustrated and described.

* * * * *